(12) United States Patent
Birdsall et al.

(10) Patent No.: US 8,205,317 B2
(45) Date of Patent: Jun. 26, 2012

(54) METHOD OF MANUFACTURING A CONTROLLED POROSITY STENT

(75) Inventors: Matthew J. Birdsall, Santa Rosa, CA (US); Jeffrey W. Allen, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 1040 days.

(21) Appl. No.: 11/778,430

(22) Filed: Jul. 16, 2007

(65) Prior Publication Data
US 2009/0024199 A1     Jan. 22, 2009

(51) Int. Cl.
*B23P 25/00* (2006.01)
*A61F 2/06* (2006.01)

(52) U.S. Cl. ............... 29/458; 29/557; 29/558; 623/1.39
(58) Field of Classification Search ............ 29/458, 29/557, 558; 623/1.39, 1.42
See application file for complete search history.

(56) References Cited

U.S. PATENT DOCUMENTS

| | | | | |
|---|---|---|---|---|
| 6,013,854 | A * | 1/2000 | Moriuchi | 623/1.11 |
| 6,253,443 | B1 * | 7/2001 | Johnson | 29/557 |
| 6,325,821 | B1 * | 12/2001 | Gaschino et al. | 623/1.15 |
| 6,805,972 | B2 * | 10/2004 | Erlebacher et al. | 428/613 |
| 7,294,409 | B2 * | 11/2007 | Lye et al. | 428/610 |
| 7,550,005 | B2 * | 6/2009 | Bates et al. | 623/1.15 |
| 7,575,593 | B2 * | 8/2009 | Rea et al. | 623/1.42 |
| 7,647,687 | B2 * | 1/2010 | Koch et al. | 29/557 |
| 7,682,388 | B2 * | 3/2010 | Rea | 623/1.42 |
| 2001/0029660 | A1 * | 10/2001 | Johnson | 29/557 |
| 2002/0019660 | A1 | 2/2002 | Gianotti et al. | |
| 2004/0040416 | A1 * | 3/2004 | Erlebacher et al. | 75/345 |
| 2004/0148015 | A1 * | 7/2004 | Lye et al. | 623/1.15 |
| 2004/0237282 | A1 * | 12/2004 | Hines | 29/527.2 |
| 2004/0247642 | A1 * | 12/2004 | Kaul et al. | 424/423 |
| 2005/0060021 | A1 | 3/2005 | O'Brien et al. | |
| 2005/0070989 | A1 * | 3/2005 | Lye et al. | 623/1.4 |
| 2005/0070990 | A1 * | 3/2005 | Stinson | 623/1.11 |
| 2005/0096733 | A1 | 5/2005 | Kovneristy et al. | |
| 2005/0251245 | A1 * | 11/2005 | Sieradzki et al. | 623/1.39 |
| 2006/0121080 | A1 * | 6/2006 | Lye et al. | 424/423 |

(Continued)

FOREIGN PATENT DOCUMENTS

GB         2425485         11/2006

(Continued)

OTHER PUBLICATIONS

Flemings, Merton "Solidification Processing" pp. 58-176.

(Continued)

*Primary Examiner* — Essama Omgba

(57) ABSTRACT

A method of manufacturing a stent includes forming a stent blank including a predetermined alloy composition, the alloy composition including at least base element and at least one sacrificial element and forming a stent framework from the stent blank. The method further includes removing at least a portion of the sacrificial element and forming at least one pore based on the removal. A method of manufacturing a vascular treatment system includes forming a stent blank including a predetermined alloy composition including at least one base element and at least one sacrificial element. The method further includes forming a stent framework and removing at least a portion of the sacrificial element. The method also includes forming at least one pore based on the removal, bending the stent framework to a delivery shape, and attaching the bent stent framework including the formed pores to a catheter.

34 Claims, 6 Drawing Sheets

U.S. PATENT DOCUMENTS

| | | | |
|---|---|---|---|
| 2006/0193886 A1* | 8/2006 | Owens et al. | 424/423 |
| 2006/0193887 A1* | 8/2006 | Owens et al. | 424/423 |
| 2006/0193888 A1* | 8/2006 | Lye et al. | 424/423 |
| 2006/0193889 A1* | 8/2006 | Spradlin et al. | 424/423 |
| 2006/0193890 A1* | 8/2006 | Owens et al. | 424/423 |
| 2006/0276877 A1* | 12/2006 | Owens et al. | 623/1.15 |
| 2006/0276878 A1* | 12/2006 | Owens et al. | 623/1.15 |
| 2006/0276879 A1* | 12/2006 | Lye et al. | 623/1.15 |
| 2006/0276884 A1* | 12/2006 | Lye et al. | 623/1.39 |
| 2006/0276885 A1* | 12/2006 | Lye et al. | 623/1.39 |
| 2007/0131318 A1* | 6/2007 | Broadley et al. | 148/556 |
| 2007/0224099 A1* | 9/2007 | Biener et al. | 423/247 |
| 2007/0296103 A1* | 12/2007 | Hayes et al. | 264/41 |
| 2008/0086198 A1* | 4/2008 | Owens et al. | 623/1.39 |
| 2008/0097591 A1* | 4/2008 | Savage et al. | 623/1.43 |
| 2008/0189928 A1* | 8/2008 | Dolan | 29/458 |
| 2008/0249599 A1* | 10/2008 | Allen et al. | 623/1.4 |
| 2009/0118823 A1* | 5/2009 | Atanasoska et al. | 623/1.49 |
| 2009/0192592 A1* | 7/2009 | Asgari | 623/1.39 |
| 2009/0196899 A1* | 8/2009 | Birdsall et al. | 424/423 |
| 2009/0228089 A1* | 9/2009 | Wilcox | 623/1.11 |
| 2009/0292352 A1* | 11/2009 | Stinson | 623/1.42 |

FOREIGN PATENT DOCUMENTS

| | | |
|---|---|---|
| WO | WO 2004043292 A2 * | 5/2004 |
| WO | WO2006/020742 | 2/2006 |

OTHER PUBLICATIONS

Rostoker, William et al. "Interpretation of Metallographic Structures" pp. 105-107.

* cited by examiner

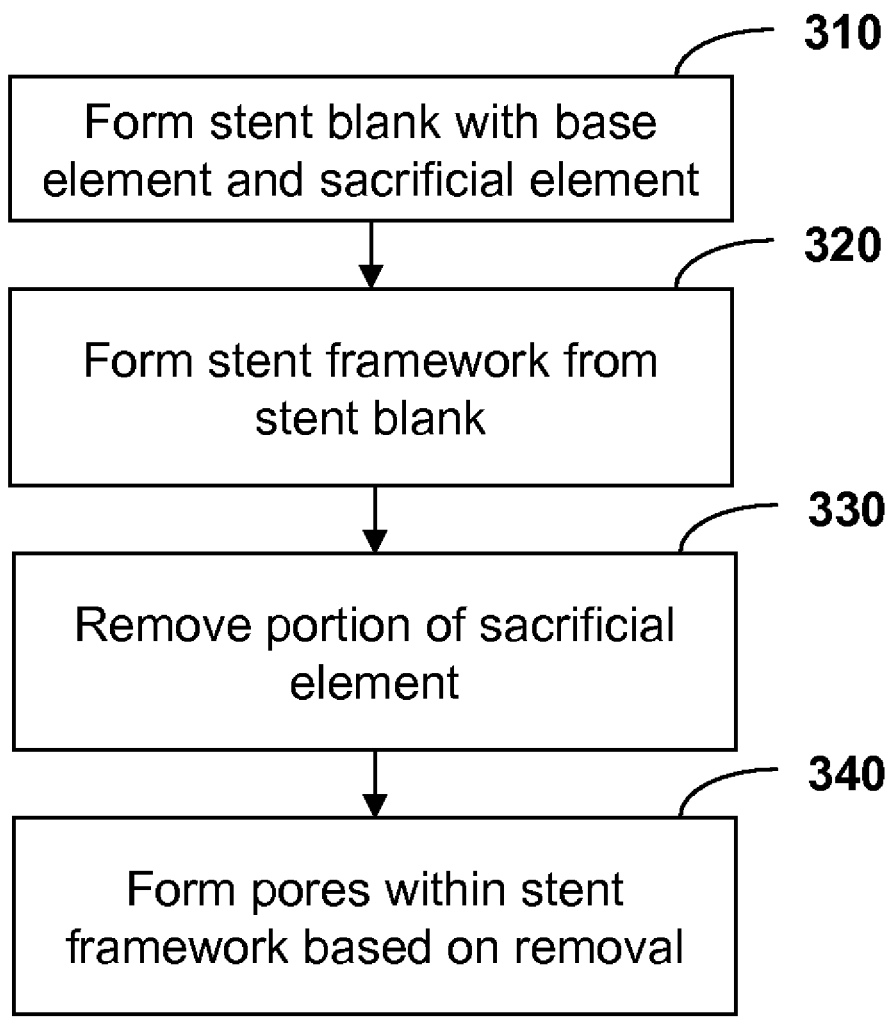

METHOD OF MANUFACTURING A CONTROLLED POROSITY STENT

TECHNICAL FIELD

This invention relates generally to medical devices for treating vascular problems, and more particularly to a stent with a controlled alloy.

BACKGROUND OF THE INVENTION

Vascular stents are commonly used to restore patency to a myriad of vessels. These stents are often deployed with a drug applied to the surface, either directly, or with a polymer. It is desirable to increase the volume of drug carried upon the stent, and previous solutions have provided for the depots, channels, pores, or similar surface modifications in an exterior surface of the stent. Typically, these modifications result from the application of a mechanical or chemical force to the surface of the stent. For example, some surface modifications are stamped onto the surface, while other stents receive a chemical bath to etch a pattern, such as with lithography.

Another prior solution includes attaching a layer of an alloyed material to a base stent, and then applying a dealloying process to the layer. As the alloyed material is dealloyed, a portion of the alloy leaches out of the material, leaving a plurality of micropores in the layer. However, this technique requires that the layer of alloyed material be joined to a base stent, and further results in formation of the desired pores solely within the alloyed layer.

It would be desirable, therefore, to overcome the limitations of the prior art.

SUMMARY OF THE INVENTION

One aspect of the present invention is a method of manufacturing a stent includes forming a stent blank including a predetermined alloy composition, the alloy composition including at least base element and at least one sacrificial element and forming a stent framework from the stent blank. The method further includes removing at least a portion of the sacrificial element and forming at least one pore based on the removal.

Another aspect of the invention provides a method of manufacturing a vascular treatment system includes forming a stent blank including a predetermined alloy composition including at least one base element and at least one sacrificial element. The method further includes forming a stent framework and removing at least a portion of the sacrificial element. The method also includes forming at least one pore based on the removal, bending the stent framework to a delivery shape, and attaching the bent stent framework including the formed pores to a catheter.

The foregoing and other features and advantages of the invention will become further apparent from the following detailed description of the preferred embodiments, read in conjunction with the accompanying drawings. The detailed description and drawings are merely illustrative of the invention, rather than limiting the scope of the invention being defined by the appended claims and equivalents thereof.

BRIEF DESCRIPTION OF THE DRAWINGS

FIG. 3 is a flow diagram of a method of manufacturing a stent, in accordance with one embodiment of the current invention;

DETAILED DESCRIPTION

The invention will now be described by reference to the drawings wherein like numbers refer to like structures.

Figure 1:
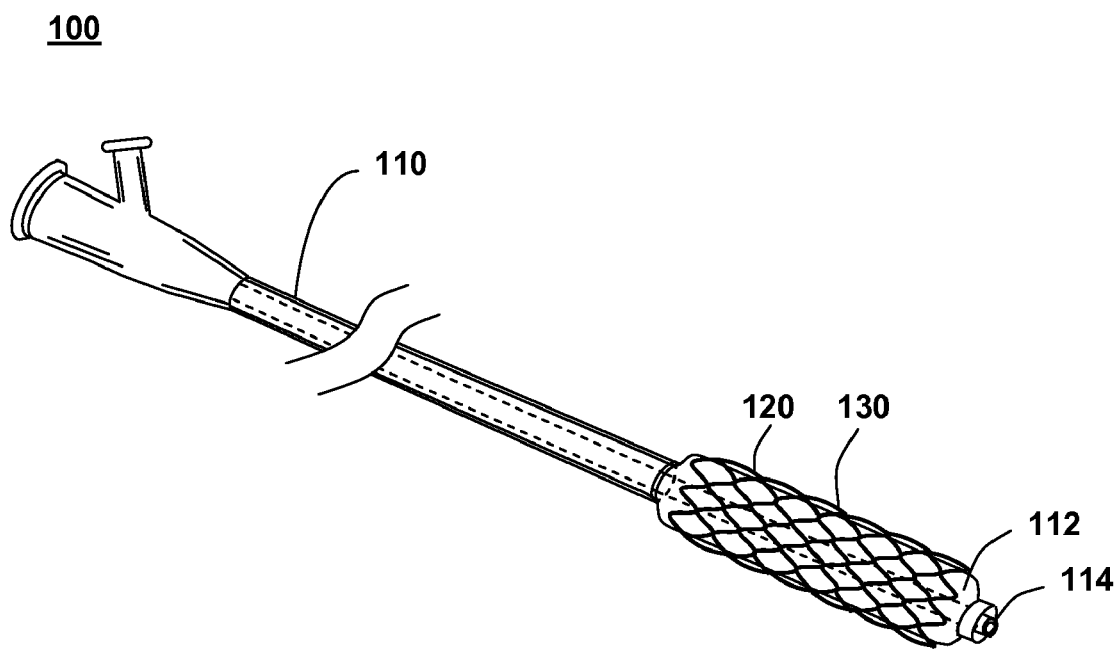
FIG. 1 is an illustration of a system for treating a vascular condition including a stent coupled to a catheter, in accordance with one embodiment of the current invention.

FIG. 1 shows an illustration of a system for treating a vascular condition, comprising a stent coupled to a catheter, in accordance with one embodiment of the present invention at 100. Stent with catheter 100 includes a stent 120 coupled to a delivery catheter 110. Stent 120 includes a stent framework 130. In one embodiment, at least one drug coating, or a drug-polymer layer, is applied to a surface of the stent framework.

Insertion of stent 120 into a vessel in the body helps treat, for example, heart disease, various cardiovascular ailments, and other vascular conditions. Catheter-deployed stent 120 typically is used to treat one or more blockages, occlusions, stenoses, or diseased regions in the coronary artery, femoral artery, peripheral arteries, and other arteries in the body. Treatment of vascular conditions may include the prevention or correction of various ailments and deficiencies associated with the cardiovascular system, the cerebrovascular system, urinogenital systems, biliary conduits, abdominal passageways and other biological vessels within the body.

The stent framework comprises an alloy comprising base elements and sacrificial elements and other substances. The sacrificial element is an element to be leached or dealloyed prior to insertion into a body lumen.

Catheter 110 of an exemplary embodiment of the present invention includes a balloon 112 that expands and deploys the stent within a vessel of the body. After positioning stent 120 within the vessel with the assistance of a guide wire traversing through a guide wire lumen 114 inside catheter 110, balloon 112 is inflated by pressurizing a fluid such as a contrast fluid or saline solution that fills a tube inside catheter 110 and balloon 112. Stent 120 is expanded until a desired diameter is reached, and then the contrast fluid is depressurized or pumped out, separating balloon 112 from stent 120 and leaving the stent 120 deployed in the vessel of the body. Alternately, catheter 110 may include a sheath that retracts to allow expansion of a self-expanding version of stent 120.

Figure 2A:
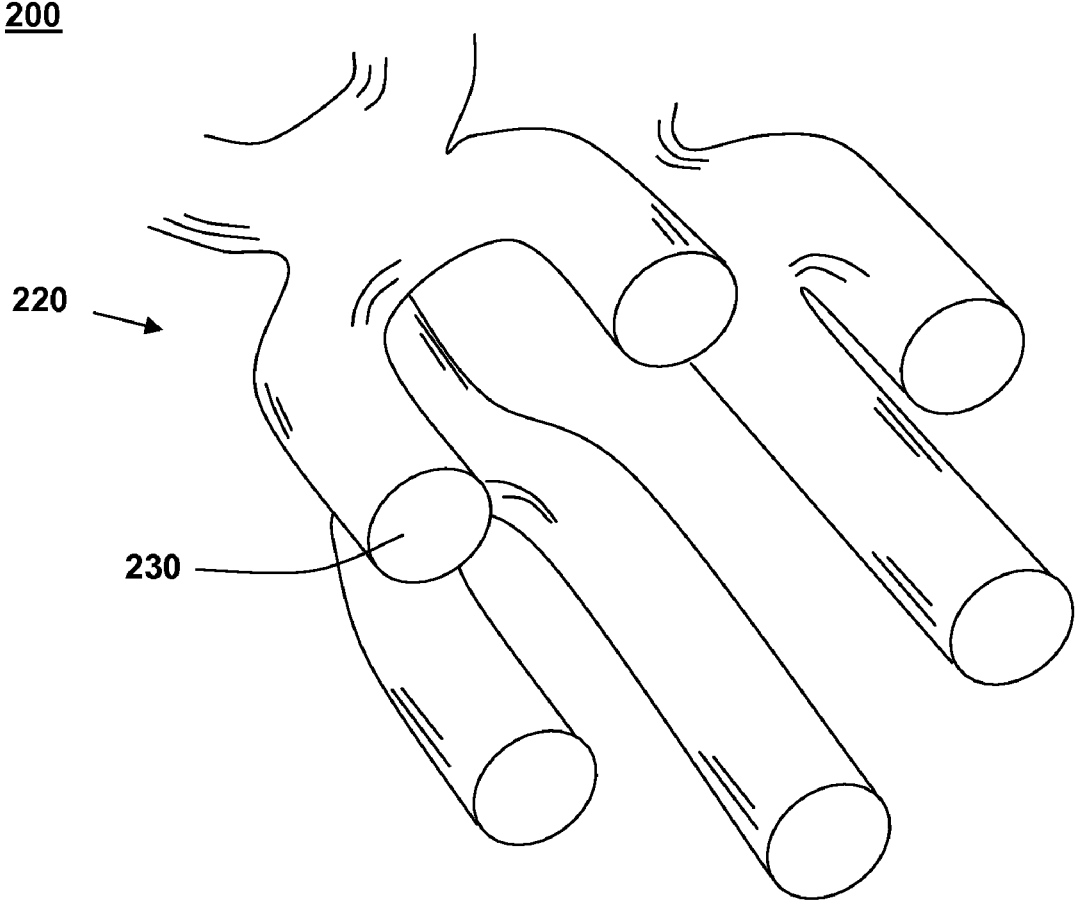
FIG. 2A is a cross-sectional perspective view of a stent framework, in accordance with one embodiment of the current invention.

FIG. 2A shows a cross-sectional perspective view of a stent, in accordance with one embodiment of the present invention at 200. A stent 220 includes a stent framework 230. FIG. 2A illustrates the stent prior to leaching of a sacrificial element from the stent framework.

Stent framework 230 comprises a metallic base formed of constituent elements, such as cobalt-chromium, stainless steel, nitinol, magnesium, tantalum, MP35N alloy, platinum, titanium, a chromium-based alloy, a suitable biocompatible alloy, a suitable biocompatible material, a biocompatible polymer, or a combination thereof. In one embodiment, the alloy does not include yttrium, neodymium, or zirconium. Either prior to attachment to a catheter, or after attachment to a catheter, a dealloying process is applied to the stent framework to remove at least a portion of the sacrificial elements from the stent framework. As the sacrificial element leaches out of the stent framework, a pore or nanopore is left in the space previously occupied by the leached sacrificial element. Tissue ingrowth into the pores may improve biocompatibility, and the volume of space defined by the pores can increase the drug carrying capacity of the stent. The distribution of the formed pores can be controlled into a desired pattern in one embodiment. For example, the formed pores can assume a particular pattern, such as sinusoid, quincunx, or other. Alternatively, the formed pores can be dispersed on only a single side of the stent, such as the side of the stent opposite a lumen formed by the stent framework. In another embodiment, the distribution of the formed pores is uncontrolled.

The stent framework can be further coated with additional layers of material, such as therapeutic agents, cap coats, polymeric layers, or the like.

In one embodiment, a drug coating is disposed on stent framework 230. In certain embodiments, the drug coating includes at least one drug layer. In other embodiments, at least one coating layer is disposed over the stent framework, and can envelop the drug coating layer. For example, the drug layer includes at least a first therapeutic agent. In one embodiment, coating layers include magnesium, or another bioabsorbable constituent. In one embodiment, the coating layers are sputter coats. In other embodiments, the magnesium coating is applied using another appropriate technique, such as vacuum deposition, dipping, or the like. In one embodiment, the coating layer is a topcoat.

Although illustrated with one set of drug layers and coating layers, multiple sets of drug and coating layers may be disposed on stent framework 230. For example, ten sets of layers, each layer on the order of 0.1 micrometers thick, can be alternately disposed on stent framework 230 to produce a two-micrometer thick coating. In another example, twenty sets of layers, each layer on the order of 0.5 micrometers thick, can be alternately disposed on stent framework 230 to produce a twenty-micrometer thick coating. The drug layers and the coating layers need not be the same thickness, and the thickness of each may be varied throughout the drug coating. In one example, at least one drug layer is applied to an outer surface of the stent framework. The drug layer can comprise a first therapeutic agent such as camptothecin, rapamycin, a rapamycin derivative, or a rapamycin analog. In another example, at least one coating layer comprises a magnesium layer of a predetermined thickness. In one embodiment, the thickness of the magnesium coating is selected based on expected leaching rates, while in other embodiments, the thickness is selected based on the drug maintained in place between the stent framework surface and the magnesium layer. In another embodiment, the thickness of the magnesium layer is variable over the length of the stent framework. Drug or magnesium elution refers to the transfer of a therapeutic agent from the drug coating to the surrounding area or bloodstream in a body. The amount of drug eluted is determined as the total amount of therapeutic agent excreted out of the drug coating, typically measured in units of weight such as micrograms, or in weight per peripheral area of the stent.

Figure 2B:
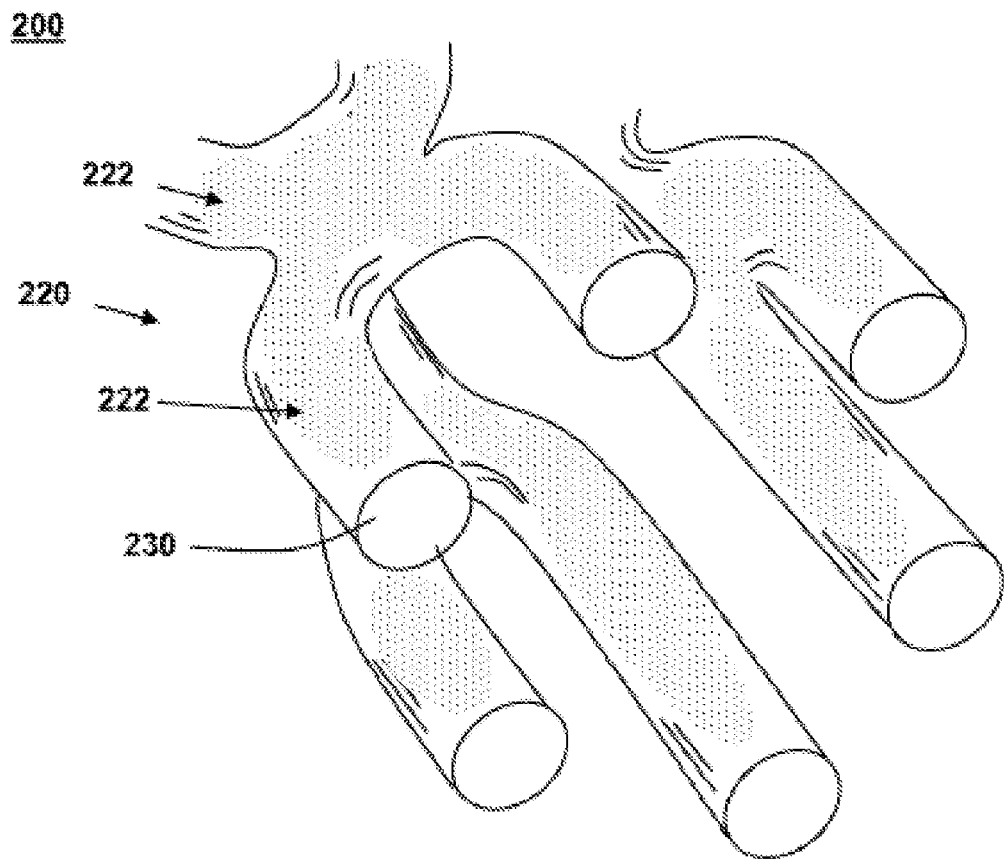
FIG. 2B is a cross-sectional perspective view of a stent framework, in accordance with one embodiment of the current invention.

FIG. 2B illustrates the stent 200 of FIG. 2A after leaching of the magnesium from the stent framework results in a plurality of pores 222 within the surface of the stent.

Figure 2C:
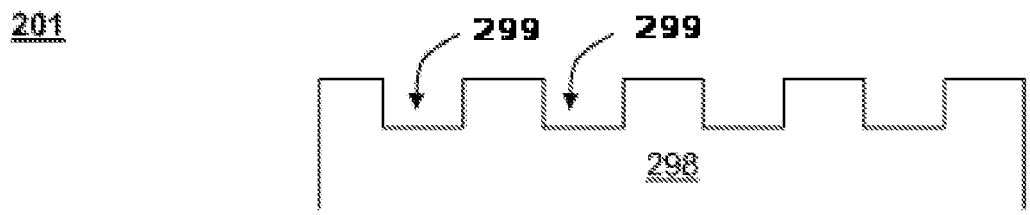
FIG. 2C is a cross-sectional perspective view of a stent framework, in accordance with one embodiment of the current invention.
Figure 4:
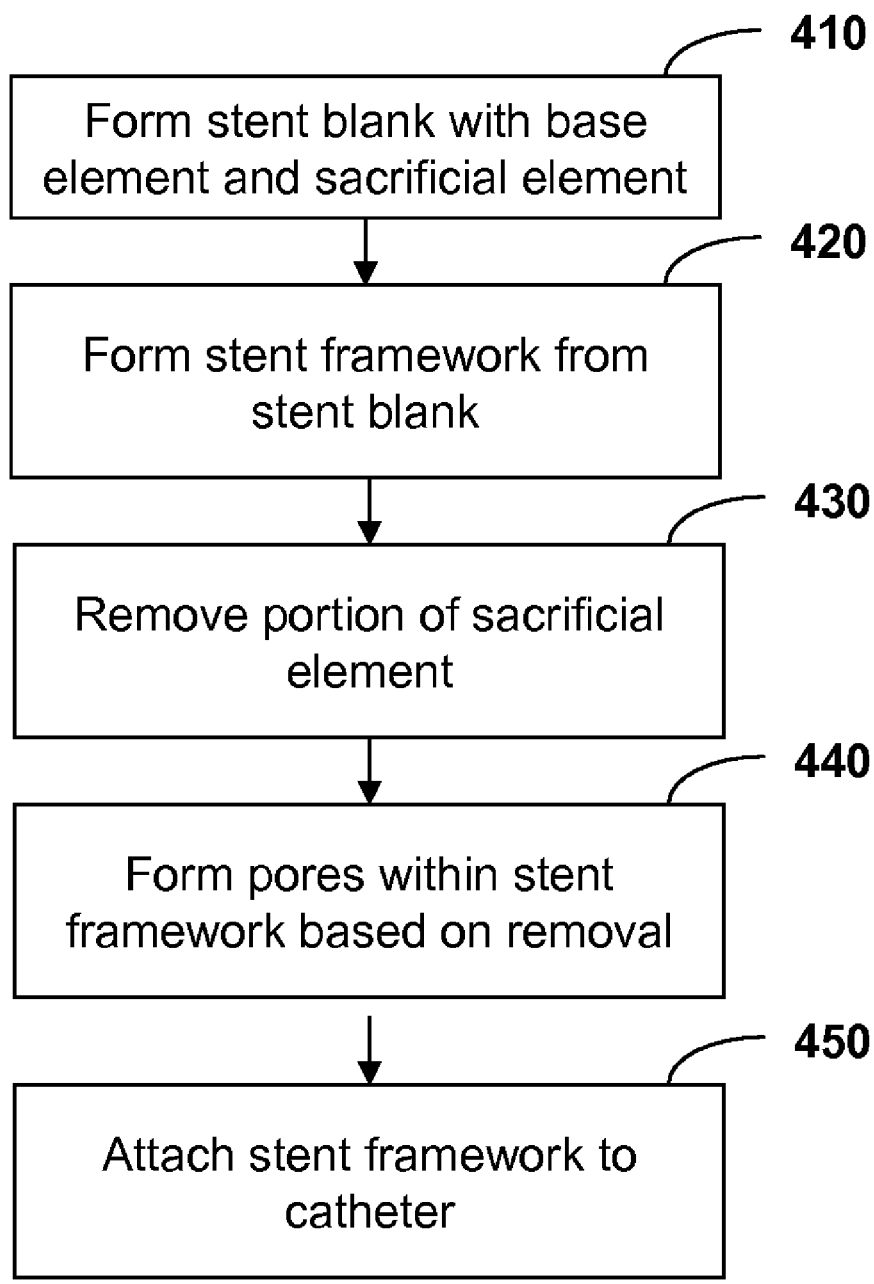
FIG. 4 is a flow diagram of a method of manufacturing a vascular treatment system, in accordance with one embodiment of the current invention.
Figure 5:
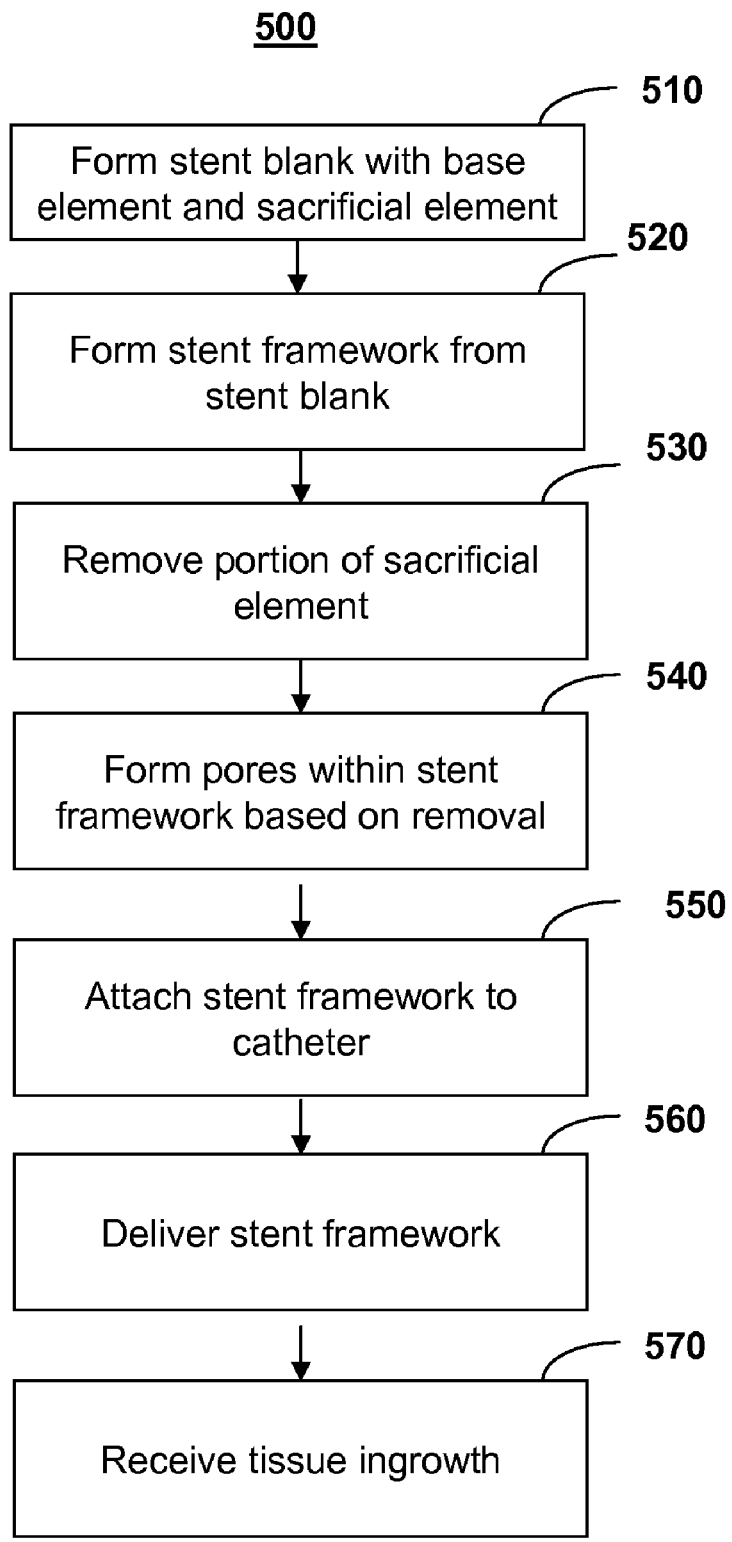
FIG. 5 is a flow diagram of a method treating a vascular condition, in accordance with one aspect of the invention.

FIGS. 2A and 2B illustrate the stent framework as substantially tubular in cross-section. However, alternate geometric arrangements are contemplated. For example, FIG. 2C illustrates a stent framework 201 cross-section using a single strut of the framework with a substantially planar construction. Stent 201 includes a framework after the sacrificial element/s has leached from magnesium-alloyed portion 298, including a plurality of pores 299. Other geometric strut configurations are also anticipated, as well as variable configurations.

FIG. 3 illustrates one embodiment of a method 300 for manufacturing a stent with nanopores, in accordance with one aspect of the invention. Method 300 begins by forming a stent blank including a predetermined alloy composition, the alloy composition including at least base element and at least one sacrificial element, at block 310. The base element includes a metallic element selected for certain physical characteristics, such as machinability, strength, or the like. For example, the base element can be stainless steel, cobalt, chromium, MP35N, nitinol, tantalum, or the like. The sacrificial element is an element selected to be leached from the combined alloy to form a plurality of pores throughout the stent framework. For example, the sacrificial element can be magnesium, phosphorus, copper, boron, silicon, zinc, carbon, or the like. In one embodiment, the base element and sacrificial element are noble metals, and the sacrificial element is a lesser noble metal than the base element. The sacrificial element is selected responsive to physical characteristics, such as melting point, machining considerations, or the like. The stent blank is formed from a molten alloy comprising the base element and sacrificial element. In one embodiment, the stent blank is an ingot. In other embodiments, the base element can be a ceramic or graphite, and the sacrificial element is driven into the base element in bulk after formation of the stent blank of the base element.

The solidification process is controlled to increase control of pore orientation during a dealloying process. As a molten alloy combination is cooled, the cooling temperature is controlled to form a cone and skin, for example. Alternatively, or in addition, the temperature is controlled to increase formation of inter-dendritic regions on a surface of the cooled alloy. In other embodiments, the temperature gradient is controlled to affect the solidification rate as well as growth of columnar or cored structures grown epitaxially on the surface of the matrix. The epitaxially grown structures are then subject to additional surface modification, such as etching or mechanical modifications to produce inter-dendritic regions includes a network of spaces, such as pores, to be filled with a therapeutic agent and/or polymer. Alternatively, a cooled ingot can be subjected to incipient melting to secure surface material characteristics in accord with a desired porosity characteristic. In such embodiments, a material with a lower melt phase can precipitate out at the surface while largely preserving structural integrity of the final product. In other embodiments, a sacrificial element is introduced into the ingot by coating and driving sacrificial elements into the bulk ingot or stent blank. In other embodiments, the alloy is subjected to a constitutional supercooling, resulting in a solute rich layer generated at the interface between alloy constituents. In other embodiments, a rapid quench during solidification increases formation of cellular structures and affects the breakdown of the planar interface near a grain boundary.

In other embodiments, the cooling process is controlled to affect the formation of plates formed between dendrite arms in the solidified grain structure. These plates can be controlled to result in abrupt concentration changes between the dendrite center and interdendritic regions, increasing the concentration of the sacrificial element within the interdendritic regions. In addition, certain embodiments of the invention further adjust quenching rates to affect the dendrite arm spacing.

In other embodiments, the alloy grains are controlled to reduce formation of dendritic arms, creating a nondendritic alloy. Such alloys have increased segregation of alloy constituents in an equiaxed region. In one such embodiment, the alloy constituents include a zirconium-refined magnesium alloy.

A stent framework is formed from the stent blank at step 320. The stent framework is formed with any appropriate machining technique, including cutting, stamping or the like. Depending on the shape of the stent to be manufactured, the stent framework can be cut from the blank, or bent into the desired shape. Other machining techniques are also appropriate, depending on the shape and alloyed material.

After forming the stent framework, at least a portion of the sacrificial element is removed from the stent framework, at step 330. In one embodiment, the sacrificial element is removed via a dealloying process. The dealloying process is determined based on the base element and sacrificial element. In one embodiment, the dealloying process includes application of inductive heat to the stent framework. In another embodiment, the dealloying process comprises application of at least one chemical reagent to the stent framework. In another embodiment, the dealloying process comprises application of at least one electrical field to the stent framework. In yet another embodiment, the dealloying process comprises application of heat to the stent framework. In another embodiment, the dealloying process comprises use of a laser. In another embodiment, the dealloying process includes use of an electron beam. In one embodiment, a mask is applied to predetermined areas of the stent framework to shield at least a portion of the stent framework from the dealloying process. For example, the crown of a stent can be masked to prevent formation of pores within the crown, an area of the stent subject to higher mechanical stress and strain than other areas. In addition, the sacrificial element can be removed throughout the entire thickness of the stent framework, or only a selected depth.

In one embodiment, the formation techniques, including the cooling of the alloy, improve the ability to dealloy the sacrificial element, such as by increasing the concentration of the sacrificial element in the interdendritic spaces of the alloy, or by increasing the interdendritic space.

As the sacrificial element is removed from the stent framework, at least one pore is formed, at step 340. As the sacrificial element exits the stent framework, the volume of space previously occupied by the sacrificial element becomes a pore.

In one embodiment, the method further includes applying at least one therapeutic agent to the stent, including the pores. In one embodiment, as the therapeutic agent is eluted from the surface of the stent on delivery, the pores receive tissue ingrowth. In embodiments without the application of the therapeutic agent, the pores may still receive tissue ingrowth.

Another aspect of the invention provides a method 400 of manufacturing a vascular treatment system. A stent is manufactured in accordance with method 300 such that steps 410, 420, 430, and 440 are implemented in a similar fashion as step 310, 320, 330, and 340. The manufactured stent is bent into a delivery shape, and then disposed, step 450, on a catheter.

Another aspect of the invention provides a method 500 of treating a vascular condition. The method for treating vascular condition includes manufacturing a stent in accordance with method 300 such that steps 510, 520, 530, and 540 are implemented in a similar fashion as step 310, 320, 330, and 340. The bent manufactured stent is bent into a delivery shape and disposed, step 550, on a catheter and delivered, step 560, to a treatment site via the catheter. The delivered stent is then deployed, and tissue ingrowth is received in the pores in step 570. In one embodiment, the method further includes applying at least one therapeutic agent to the manufactured stent, either before or after bending, and either before or after applying the stent to the catheter, but prior to delivery to the treatment site. The therapeutic agent is then eluted from the stent.

As used herein, the term 'therapeutic agent' includes a number of pharmaceutical drugs that have the potential to be used in drug, or drug-polymer coatings. For example, an antirestenotic agent such as rapamycin prevents or reduces the recurrence of narrowing and blockage of the bodily vessel. An antisense drug works at the genetic level to interrupt the process by which disease-causing proteins are produced. An antineoplastic agent is typically used to prevent, kill, or block the growth and spread of cancer cells in the vicinity of the stent. An antiproliferative agent may prevent or stop targeted cells or cell types from growing. An antithrombogenic agent actively retards blood clot formation. An anticoagulant often delays or prevents blood coagulation with anticoagulant therapy, using compounds such as heparin and coumarins. An antiplatelet agent may be used to act upon blood platelets, inhibiting their function in blood coagulation. An antibiotic is frequently employed to kill or inhibit the growth of microorganisms and to combat disease and infection. An anti-inflammatory agent such as dexamethasone can be used to counteract or reduce inflammation in the vicinity of the stent. At times, a steroid is used to reduce scar tissue in proximity to an implanted stent. A gene therapy agent may be capable of changing the expression of a person's genes to treat, cure or ultimately prevent disease.

By definition, a bioactive agent is any therapeutic substance that provides treatment of disease or disorders. An organic drug is any small-molecule therapeutic material. A pharmaceutical compound is any compound that provides a therapeutic effect. A recombinant DNA product or a recombinant RNA product includes altered DNA or RNA genetic material. Bioactive agents of pharmaceutical value may also include collagen and other proteins, saccharides, and their derivatives. The molecular weight of the bioactive agent typically ranges from about 200 to 60,000 Dalton and above.

It is important to note that the figures herein illustrate specific applications and embodiments of the present invention, and are not intended to limit the scope of the present disclosure or claims to that which is presented therein. Upon reading the specification and reviewing the drawings hereof, it will become immediately obvious to those skilled in the art that many other embodiments of the present invention are possible, and that such embodiments are contemplated and fall within the scope of the presently claimed invention without departing from the spirit and scope of the invention. The scope of the invention is indicated in the appended claims, and all changes that come within the meaning and range of equivalents are intended to be embraced therein.

We claim:

1. A method of manufacturing a stent comprising:
   melting at least one base element with at least one sacrificial element to form a molten alloy;
   forming the molten alloy into a stent blank having a predetermined alloy composition of the at least one base element and the at least one sacrificial element;
   forming a stent framework from the stent blank;
   attaching the stent framework to a catheter;
   removing at least a portion of the sacrificial element from the stent framework; and
   forming at least one pore based on the removing;
   wherein the attaching is performed before the removing, and forming the molten alloy into a stent blank comprises controlling cooling temperature as the molten alloy cools to increase formation of inter-dendritic regions on a surface of the stent blank.

2. The method of claim 1 further comprising applying at least one therapeutic agent to the pore.

3. The method of claim 1 wherein removing the at least a portion of the sacrificial element comprises a dealloying process.

4. The method of claim 3 wherein the dealloying process comprises a process selected from the group consisting of application of inductive heat to the stent framework, application of at least one chemical reagent to the stent framework, and application of heat to the stent framework.

5. The method of claim 3 wherein the dealloying process comprises application of at least one electrical field to the stent framework.

6. The method of claim 1 wherein the sacrificial element is magnesium and further comprising a magnesium coating layer disposed on the stent framework.

7. The method of claim 1 wherein the stent framework has a crown, the method further comprising applying a mask to the crown before the removing.

8. The method of claim 1 wherein the removing comprises removing at least a portion of the sacrificial element through an entire thickness of the stent framework.

9. The method of claim 1 wherein the stent blank is an ingot.

10. The method of claim 1 wherein the forming the molten alloy into a stent blank further comprises controlling temperature gradient as the molten alloy cools to grow colander structures epitaxially on the surface of the stent blank.

11. The method of claim 1 wherein the forming the molten alloy into a stent blank further comprises:
  forming a cooled ingot from the molten alloy; and
  subjecting the cooled ingot to incipient melting to secure surface material characteristics in accordance with desired porosity characteristics.

12. The method of claim 1 wherein the forming the molten alloy into a stent blank further comprises:
  forming an ingot from the molten alloy; and
  driving sacrificial elements into the ingot.

13. The method of claim 1 wherein the forming the molten alloy into a stent blank further comprises subjecting the molten alloy to constitutional super cooling to generate a solute rich layer at an interface between alloy constituents.

14. The method of claim 1 wherein the forming the molten alloy into a stent blank further comprises solidifying the molten alloy with a rapid quench to increase formation of cellular structures.

15. The method of claim 1 wherein the forming the molten alloy into a stent blank further comprises controlling cooling of the molten alloy to affect formation of plates between dendrite arms.

16. The method of claim 1 wherein the forming the molten alloy into a stent blank further comprises controlling quenching rates of the molten alloy to affect dendrite arms spacing.

17. The method of claim 1 wherein the forming the molten alloy into a stent blank further comprises controlling alloy grains to reduce formation of dendritic arms.

18. A method of manufacturing a stent comprising:
  melting at least one base element with at least one sacrificial element to form a molten alloy;
  forming the molten alloy into a stent blank having a predetermined alloy composition of the at least one base element and the at least one sacrificial element;
  forming a stent framework from the stent blank;
  attaching the stent framework to a catheter;
  removing at least a portion of the sacrificial element from the stent framework; and
  forming at least one pore based on the removing;
  wherein the attaching is performed before the removing, and the forming the molten alloy into a stent blank comprises controlling temperature gradient as the molten alloy cools to grow colander structure epitaxially on a surface of the stent blank.

19. The method of claim 18 further comprising applying at least one therapeutic agent to the pore.

20. The method of claim 18 wherein removing the at least a portion of the sacrificial element comprises a dealloying process.

21. The method of claim 20 wherein the dealloying process comprises a process selected from the group consisting of application of inductive heat to the stent framework, application of at least one chemical reagent to the stent framework, and application of heat to the stent framework.

22. The method of claim 20 wherein the dealloying process comprises application of at least one electrical field to the stent framework.

23. The method of claim 18 wherein the sacrificial element is magnesium and further comprising a magnesium coating layer disposed on the stent framework.

24. The method of claim 18 wherein the stent framework has a crown, the method further comprising applying a mask to the crown before the removing.

25. The method of claim 18 wherein the removing comprises removing at least a portion of the sacrificial element through an entire thickness of the stent framework.

26. The method of claim 18 wherein the stent blank is an ingot.

27. The method of claim 18 wherein the forming the molten alloy into a stent blank further comprises controlling cooling temperature as the molten alloy cools to increase formation of inter-dendritic regions on the surface of the stent blank.

28. The method of claim 18 wherein the forming the molten alloy into a stent blank further comprises:
  forming a cooled ingot from the molten alloy; and
  subjecting the cooled ingot to incipient melting to secure surface material characteristics in accordance with desired porosity characteristics.

29. The method of claim 18 wherein the forming the molten alloy into a stent blank further comprises:
  forming an ingot from the molten alloy; and
  driving sacrificial elements into the ingot.

30. The method of claim 18 wherein the forming the molten alloy into a stent blank further comprises subjecting the molten alloy to constitutional super cooling to generate a solute rich layer at an interface between alloy constituents.

31. The method of claim 18 wherein the forming the molten alloy into a stent blank further comprises solidifying the molten alloy with a rapid quench to increase formation of cellular structures.

32. The method of claim 18 wherein the forming the molten alloy into a stent blank further comprises controlling quenching rates of the molten alloy to affect formation of plates between dendritic arms.

33. The method of claim 18 wherein the forming the molten alloy into a stent blank further comprises controlling quenching rates of the molten alloy to affect dendritic arms spacing.

34. The method of claim 18 wherein the forming the molten alloy into a stent blank further comprises controlling alloy grains to reduce formation of dendritic arms.

* * * * *